(12) United States Patent
Paprocki et al.

(10) Patent No.: US 9,782,566 B1
(45) Date of Patent: Oct. 10, 2017

(54) BEND LIMITING ACCESS SHEATH

(75) Inventors: Loran J. Paprocki, St. Louis Park, MN (US); Stuart J. Lind, Edina, MN (US)

(73) Assignee: Annex Medical, Inc., Minnetonka, MN (US)

(*) Notice: Subject to any disclaimer, the term of this patent is extended or adjusted under 35 U.S.C. 154(b) by 90 days.

(21) Appl. No.: 12/387,397

(22) Filed: May 1, 2009

Related U.S. Application Data

(60) Provisional application No. 61/126,060, filed on May 1, 2008.

(51) Int. Cl.
| | | |
|---|---|---|
| *A61F 2/04* | (2013.01) | |
| *A61M 25/00* | (2006.01) | |
| *A61M 25/01* | (2006.01) | |
| *A61B 1/303* | (2006.01) | |
| *A61B 1/307* | (2006.01) | |
| *A61B 17/34* | (2006.01) | |

(52) U.S. Cl.
CPC ..... *A61M 25/0138* (2013.01); *A61B 17/3417* (2013.01); *A61B 17/3421* (2013.01); *A61B 17/3423* (2013.01); *A61F 2/042* (2013.01); *A61M 25/0041* (2013.01); *A61M 25/0133* (2013.01); *A61B 1/303* (2013.01); *A61B 1/307* (2013.01); *A61B 2017/345* (2013.01)

(58) Field of Classification Search
CPC . A61B 1/0011; A61B 1/0055; A61B 17/0057; A61B 17/3417; A61B 17/3421; A61B 17/3423; A61B 2017/00292; A61B 2017/003; A61B 2017/00305; A61B 2017/00309; A61B 2017/00314; A61B 2017/00318; A61B 2017/00331; A61B 2017/00336; A61B 2017/3425; A61B 2017/3427; A61B 2017/345; A61B 2017/3452; A61M 25/0133; A61M 25/0136; A61M 25/0138; A61M 25/0141; A61M 25/0144; A61M 25/0147; A61M 25/0152; A61M 25/00; A61M 25/0041; A61F 2/04; A61F 2/042; A61F 2/047; A61F 2/048
USPC ......... 600/114, 121–125, 138, 139, 141, 142
See application file for complete search history.

(56) References Cited

U.S. PATENT DOCUMENTS

| | | | |
|---|---|---|---|
| 3,162,214 A | | 12/1964 | Bazinet |
| 3,674,014 A | | 7/1972 | Tillander |
| 4,685,895 A | * | 8/1987 | Hatten ........................... 464/19 |
| 4,802,461 A | * | 2/1989 | Cho ............................ 600/108 |
| 4,955,384 A | | 9/1990 | Taylor et al. |
| 5,083,549 A | * | 1/1992 | Cho et al. ..................... 600/108 |
| 5,199,417 A | * | 4/1993 | Muller ..................... A61B 1/07 600/128 |
| 5,325,845 A | * | 7/1994 | Adair ........................... 600/114 |
| 5,381,782 A | | 1/1995 | DeLaRama et al. |
| 5,409,453 A | * | 4/1995 | Lundquist .......... A61B 10/0233 604/22 |

(Continued)

*Primary Examiner* — Ryan Henderson
(74) *Attorney, Agent, or Firm* — Patterson Thuente Pedersen, P.A.

(57) ABSTRACT

The present invention is an access sheath comprising a tube or sheath with a passageway primarily for endoscopic procedures accessing the ureter through the bladder. The sheath has a bend limiting feature to limit the bend angle or bend radius. The sheath exhibits flexibility up to this limit at which point it becomes rigid. Excessive force is required to bend the sheath beyond the bend limit and would result in the kinking of the tubular frame.

24 Claims, 9 Drawing Sheets

(56) References Cited

U.S. PATENT DOCUMENTS

| | | |
|---|---|---|
| 5,573,520 A | 11/1996 | Schwartz et al. |
| 5,595,186 A * | 1/1997 | Rubinstein et al. .......... 600/567 |
| 5,681,263 A | 10/1997 | Flesch |
| 5,833,632 A | 11/1998 | Jacobsen et al. |
| 5,922,443 A * | 7/1999 | Larsen et al. ................. 428/217 |
| 5,931,830 A | 8/1999 | Jacobsen et al. |
| 5,964,756 A | 10/1999 | McGaffigan et al. |
| 6,238,389 B1 * | 5/2001 | Paddock ............ A61B 18/1477 600/146 |
| 6,273,876 B1 * | 8/2001 | Klima et al. .................. 604/264 |
| 6,638,275 B1 | 10/2003 | McGaffigan et al. |
| 6,682,493 B2 | 1/2004 | Mirigian |
| 6,921,397 B2 | 7/2005 | Corcoran et al. |
| 7,413,563 B2 | 8/2008 | Corcoran et al. |
| 2004/0106852 A1 * | 6/2004 | Windheuser et al. ........ 600/125 |
| 2005/0080400 A1 * | 4/2005 | Corcoran et al. ............. 604/523 |
| 2005/0137501 A1 | 6/2005 | Euteneuer et al. |
| 2007/0179496 A1 * | 8/2007 | Swoyer .............. A61B 18/1492 606/41 |
| 2009/0182416 A1 * | 7/2009 | Forster .................. A61F 2/2427 623/2.11 |
| 2010/0160735 A1 * | 6/2010 | Bakos .......................... 600/141 |

\* cited by examiner

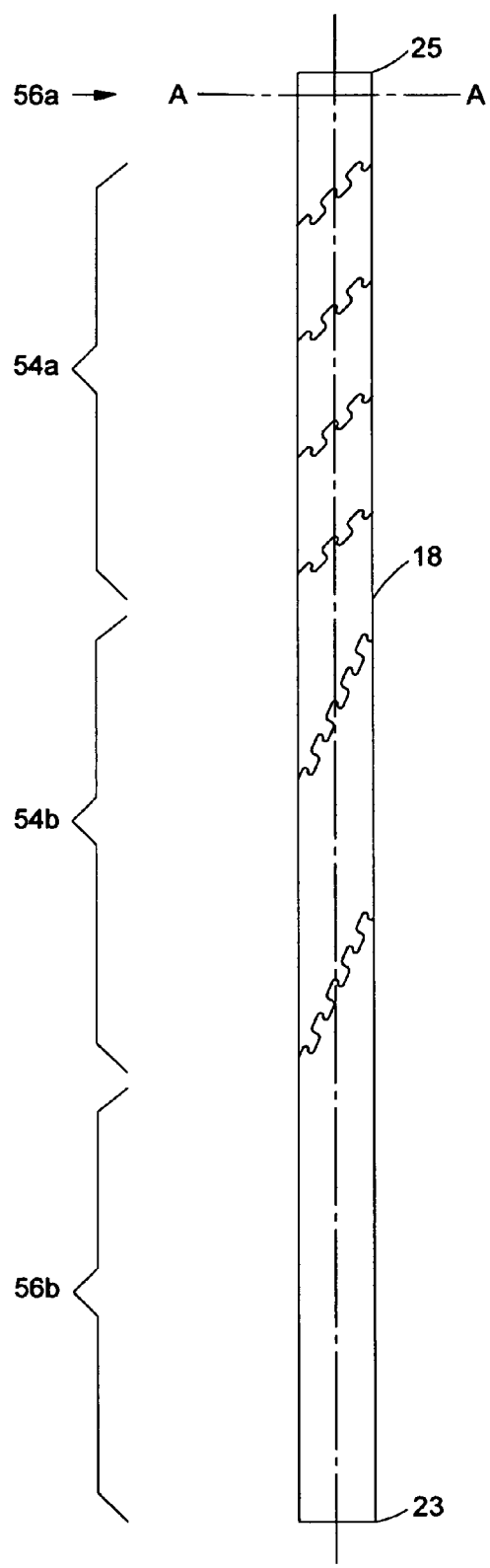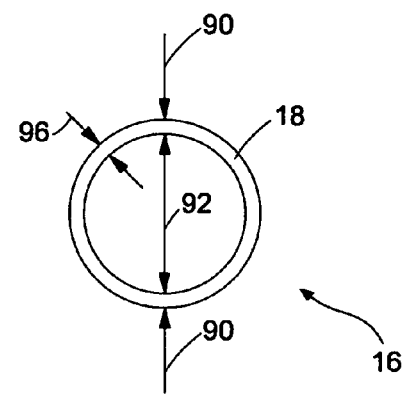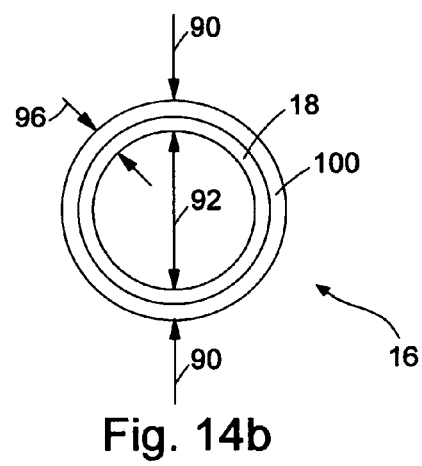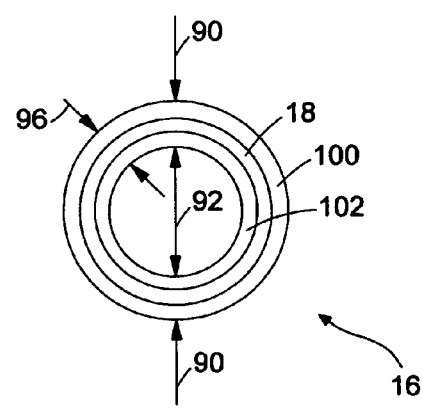
Fig. 14
Fig. 14a
Fig. 14b
Fig. 14c

COMPARISON OF THE INVENTION TO ACCESS SHEATHS MADE BY MAJOR MANUFACTURERS

| Manufacturer | Model | I.D. of distal section (Fr) | O.D. of distal section (Fr) | Sheath Length (cm) | Distal Wall Thickness | Sheath Construction |
|---|---|---|---|---|---|---|
| Boston Scientific | Navigator | 11 | 13 | 28 to 46 | ~.013" | SS coil reinforced polymeric sheath |
|  |  | 13 | 15 | 28 to 46 | * |  |
| Cook | Flexor | 9.5 | * | 13 to 55 | * | SS coil reinforced polymeric sheath |
|  |  | 12.0 | 14 | 13 to 55 | ~.014" |  |
|  |  | 14.0 | * | 20 to 55 | * |  |
| Gyrus-ACMI | UroPass | 12 | 14 | 24 to 54 | ~.011" | SS coil reinforced polymeric sheath |
| Applied Medical | Forte | 10 | 12 | 20 to 55 | * | SS coil reinforced polymeric sheath |
|  |  | 12 | 14 | 20 to 55 | ~.019" | Stepped OD increases at the proximal end |
|  |  | 14 | 16 | 20 to 35 | * |  |
| Annex Medical | Invention | 11 | 12 | 20 to 55 | .004" to .010" | Bend limiting tubular frame (uncoated or light surface coating) |
|  |  | 12 | 13 | 20 to 55 |  |  |
| Annex Medical | Invention | 12 to 13 | 14 | 20 to 55 | .006" to .011" | Bend limiting tubular frame (coated) |
|  |  | 14 to 15 | 16 | 20 to 55 |  |  |

*Unknown quantity

Fig. 15

BEND LIMITING ACCESS SHEATH

This application claims priority to U.S. Provisional Application No. 61/126,060 filed May 1, 2008, which is incorporated herein by reference in its entirety.

FIELD OF THE INVENTION

The present invention relates generally to medical devices for surgical access. More particularly, the present invention relates to surgical access devices for introduction of endoscopic surgical instrumentation into the ureter.

BACKGROUND OF THE INVENTION

Access sheaths are commonly used to establish an accessible, minimally invasive passageway into the body to facilitate and expedite the insertion and removal of devices. Once access is established, devices can be passed through the access sheath and to the treatment site with increased speed and minimized patient trauma. For instance, typical kidney stone retrieval procedures require multiple insertions and removals of the stone basket and endoscope as successive stone fragments are captured. The access sheath protects the ureter from sharp points or jagged edges of the stone fragments as they are pulled from the ureter or kidney. The access sheath also provides the physician with an established pathway into the ureter avoiding the need to re-establish that path from the urethera through the bladder and into the ureter for each insertion of the endoscope. Thus the procedure is less traumatic to the patient while being easier and faster for the physician.

Due to the nature of their use, access sheaths need to be flexible to follow patient anatomy, provide a maximized working channel for the physician, and be robust enough to confidently endure manipulation. Prior art access sheaths have been constructed with a thin-walled polymer tube. While this construction allows for a flexible access sheath with a maximized working channel, devices of this type are susceptible to kinking, elongation, and ovalization. Kinking and ovalization may render the access sheath useless since instruments may no longer be able to pass through the access sheath to the target anatomy. Furthermore, kinking may cause trauma to the patient or damage to the instruments being used.

Some known prior art access sheaths, such as U.S. Pat. No. 7,005,026, solve the kinking problem by re-inforcing the wall with a wire or wires. In Applied Medical literature, the access sheath is shown tied in a knot to highlight the catheter's extreme kink resistance. While this makes the sheath more resistant to kinking, elongation and ovalization, it increases the thickness of the sheath wall. The increased wall thickness either reduces the working channel, increases the outside diameter or both.

Reduction of the working channel is undesirable for several reasons. In many procedures multiple instruments are needed to be placed at the target anatomy simultaneously, thus requiring a maximized working channel for their placement. Also, in a kidney stone retrieval procedure reducing the access sheath inner diameter may prohibit the extraction of larger stones that would otherwise be extractable through a larger working channel.

Increasing the outer diameter of the access sheath is also undesirable. As the diameter of the access sheath increases it dilates and distends the adjacent anatomy. For instance, in a urological procedure the access sheath can split the patient's ureter if the access sheath's outer diameter is too large. Similar trauma may be caused when entering other patient vasculature.

Another problem with kink resistant, reinforced walls is that they over-bend in the bladder when being pushed up the ureter for the initial placement or when repositioning in the middle of the procedure. This tendency to over-flex and loop into the bladder is common. The bladder is a big open space that does not provide any side support for the access sheath. Once it over bends in the bladder the tip can not be pushed into the ureter. A similar effect can be seen by pushing a straightened finger directly against a wall. It is easiest to push (transmit force to the wall) with a straight finger (0° bend) or a moderately bent finger (up to 90° bend). At 180° bend it is very difficult to place force on the wall.

Whereas manufacturers laud the ability of their access sheaths to bend 360°, it can be seen in the above text that what is needed is an access sheath which is flexible enough to accommodate anatomical bends while being pushable. In addition, an access sheath should accomplish this while maximizing the working channel.

SUMMARY OF THE INVENTION

The present invention is an access sheath comprising a tube or sheath with a passageway primarily for endoscopic procedures accessing the ureter through the bladder. The sheath has a bend limiting feature to limit the bend angle or bend radius. The sheath exhibits flexibility up to this limit at which point it becomes rigid. Excessive force is required to bend the sheath beyond the bend limit and would result in the kinking of the tubular frame.

In preferred embodiments, the sheath is a tubular frame or has a tubular frame that comprises the bend limiting feature that limits the bend angle or bend radius. Preferably, at least a portion of the tubular frame is formed from a rigid material having a slot or slots at different longitudinal locations to create a bend limit.

Current access sheaths have polymeric sheaths with wire-reinforced walls that are highly kink resistant. These sheaths easily bend more than 360° without kinking. This hyper-deflectibility decreases the ability of the access sheath to be advanced through open anatomy that does not support the sheath wall into a tight lumen offering resistance. In the case of ureteral access, the sheath must have some flex to match the turns as it passes from the urethra through the bladder and into the ureter. As the access sheath is inserted into the ureteral orifice, resistance is encountered. The longitudinal force applied at the proximal end of the access sheath will result in over-bending or looping of the access sheath's shaft in the bladder. A 180° bend renders advancement impossible. The procedure is delayed as the physician must retract the access sheath and retry placement of the sheath.

This extreme deflectibility of existing access sheaths also causes the access sheath to fully conform to the patient's anatomy. In some cases, the patient's anatomy may be tortuous. The fact that current access sheaths match the anatomical tortuosity causes the medical devices passing through it to follow the same tortuous path. It should be noted that patient anatomy has a fleshy flexibility which may be partly straightened to provide a more direct pathway.

The present invention overcomes these problems by providing a sheath with flexibility at low bends but which can not exceed a specific bend limit. The present invention exhibits the flexibility required to flex from the urethra, through the bladder and into the ureter. However, as the present invention flexes to its maximum bend radius or bend angle, the access sheath stiffens and allows a more effective longitudinal transmission of force. The more effective transmission of longitudinal force to the tip allows the invention to pass the ureteral orifice and enter the ureter with greater ease. The present invention's lower bend angle or bend radius also speeds the passage of instruments and protects them from breakage due to over bending.

In one embodiment, the present invention provides an access sheath with a rigid section and a bend limiting flexible section. As mentioned previously the bend limiting feature of the present invention allows navigation of the anatomy. The incorporation of a rigid section can create a straight passageway through highly compliant tissue such as a urethra.

In one embodiment, the present invention provides an access sheath having a thin wall. Conflicting demands made on medical devices include the desire to minimize the outer diameter while increasing the inner diameter. Decreasing the outer diameter of an access sheath is desired in order to minimize the trauma to the patient as the sheath enters and potentially enlarges the tissue through which it passes. In extreme cases, a vessel may be split due to an access sheath which is too large for the anatomy through which it passes. Meanwhile the inner diameter is desired to be as large as possible so that multiple pieces of medical instrumentation may be inserted or so that irrigation may be increased. The increase in inner diameter and decrease in outer diameter ultimately results in an optimized access sheath with the thinnest wall still able to perform all other required functions. Currently available access sheaths incorporate wire reinforced polymeric tubes to form the shaft of their devices. The invention incorporates a slotted tube which could be fabricated from a thin metallic wall having a decreased thickness. The invention's tubular frame provides for the possibility of thinner walls, yet is still able to perform all other required functions.

In one embodiment, the present invention provides an access sheath having a guidewire retention feature. Guidewires are commonly used in medical procedures. This includes guidewires with lubricious coatings that facilitate the easy advancement of the guidewire through patient anatomy. A typical problem faced by physicians is the tendency of guidewires to back-out of the patient during a procedure causing loss of access to the target anatomy. The present invention incorporates a guidewire retention feature into its hub which allows the guidewire to be retained without requiring an external retention method.

The present invention also provides an access sheath having a tubular frame and coating combination that can improve lubricity and change the flexibility. Lubricious coatings on the outside surface ease the insertion of the access sheath. Likewise, lubricious coatings on the inner surface of the access sheath allow for easy passage of other medical instruments as they access the target anatomy. Polymeric coatings within the slots or on the ID or on the OD of the tubular frame will change the flexibility of the sheath, which may be beneficial in some situations.

Further objects and advantages of preferred embodiments of the device described herein are such that preferred embodiments are safe, reliable, and easy to use. Still further objects and advantages will become apparent from a consideration of the ensuing description and drawings.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention.

FIG. 14 is a longitudinal view showing another embodiment of the tubular frame or sheath shown in FIGS. 1, 3, 6 and 7.

FIG. 14a is an enlarged cross-sectional view of FIG. 14 taken at line A-A showing an embodiment without coating (uncoated).

FIG. 14b is another embodiment of FIG. 14a showing a coated outer diameter.

FIG. 14c is another embodiment of FIG. 14a showing a coated inner diameter and a coated outer diameter.

FIG. 15 is a table showing the features of major currently marketed access sheaths compared to the invention.

DETAILED DESCRIPTION OF PREFERRED EMBODIMENTS

Figure 1:
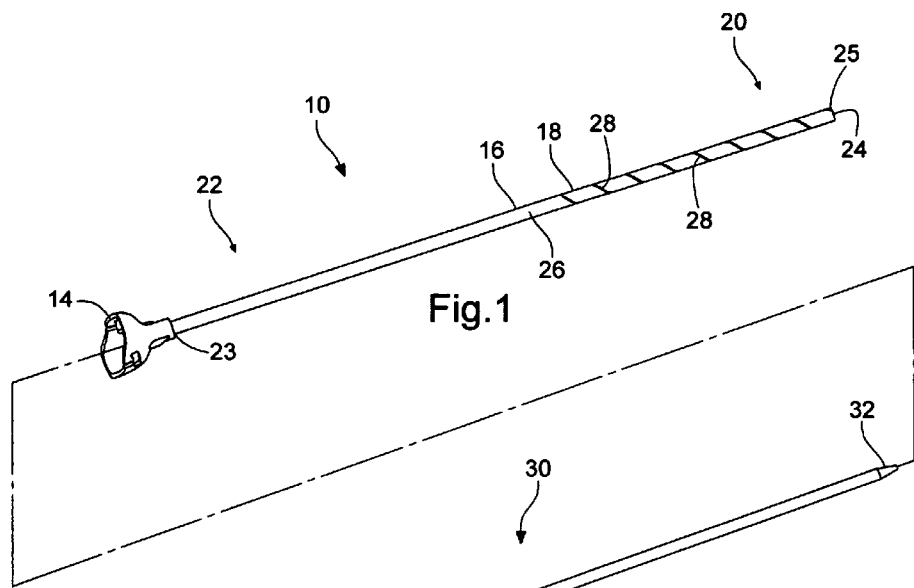
FIG. 1 is an isometric view of an embodiment of the present invention.

FIG. 1 shows an access sheath 10 that consists of a hub 14 and a tube or sheath 16. The access sheath 10 generally consists of a distal section 20 which may be positioned within a patient, and a proximal section 22 with proximal end 23 into which other medical devices may be introduced. A hub 14 is located at the proximal section 22 to facilitate the insertion of medical devices. The tube or sheath 16 includes a tubular frame 18 that surrounds an internal passageway 26 leading from the hub 14 at proximal end 23 of the proximal section 22 to the opening 24 at the distal end 25 of the distal section 20. The sheath length in FIG. 1 is the distance between 23 and 25. By the use of this passageway 26, other medical devices may gain access to, and retrieval from, the interior of the patient. One use is the removal of stones from a patient's kidney. In that procedure an endoscope visualizes stones in the kidney so that they may be captured with a stone basket. The stone, stone basket and endoscope are then retracted through the access sheath 10. The stone is removed from the basket so that the endoscope and basket may return to the kidney and repeat the procedure for additional stones.

In the distal section 20 of the access sheath 10, one or more slots 28 are cut in a generally helical orientation through the wall of the tube. Details of the path of the slot 28 are too small to be conveyed in FIG. 1. Their form and function will be discussed later in greater detail. Generally the slots 28 allow limited flexure of the distal section 20 of the access sheath 10.

Figure 2:
FIG. 2 is an isometric view of the dilator or obturator that is used in conjunction with the invention shown in FIG. 1.

FIG. 2 shows a dilator or obturator 30. The dilator or obturator 30 generally consists of proximal end and a distal end with a tube or shaft in between. A knob 34 is located at the proximal end and a tapered tip 32 exists at the distal end. Between the distal and proximal ends there exists a tube or shaft which is somewhat longer than the tube 16 of the access sheath 10, but with a smaller outer diameter. The dilator or obturator 30 may include an internal lumen for the passage of a guidewire. The dilator or obturator 30 may be attached to the access sheath 10 by the insertion of the dilator or obturator's tube or shaft through the passageway 26 of the access sheath 10.

Figure 3:
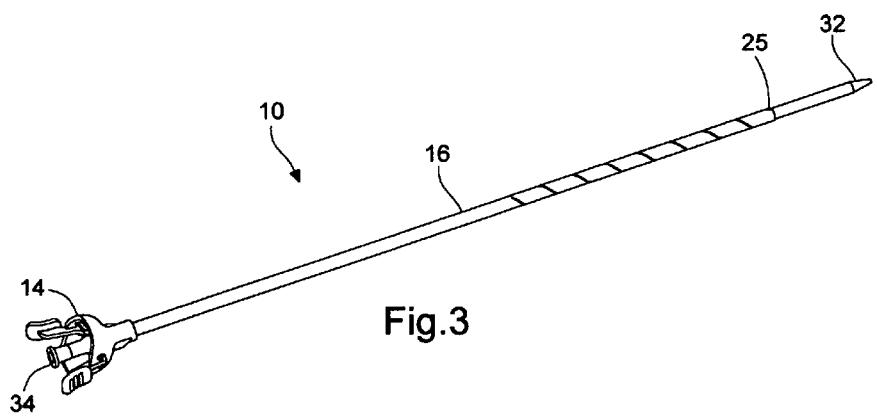
FIG. 3 is an isometric view of the dilator or obturator from FIG. 2 inserted into the access sheath shown in FIG. 1.

FIG. 3 shows a dilator or obturator 30 fully engaged with the access sheath 10. When fully attached, the tapered tip 32 of the dilator or obturator 30 extends distal to the opening 24 to ease the insertion of the access sheath 10 into patient anatomy. Once the access sheath 10 is in the desired location, the dilator or obturator 30 may be removed to enable the use of the passageway 26 by other medical instrumentation.

Figure 4:
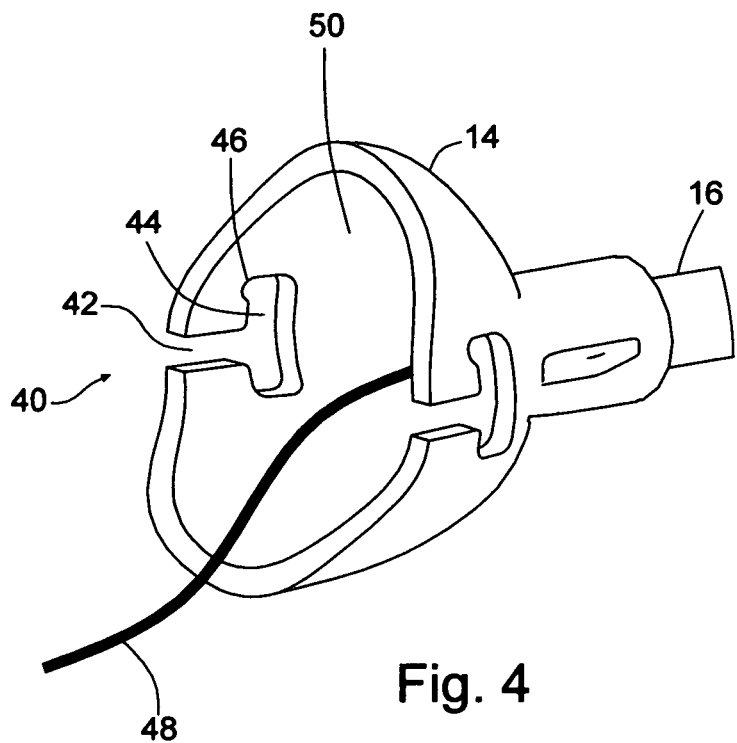
FIG. 4 is an enlarged isometric view of the proximal end of FIG. 1 with a guidewire to show an embodiment of the present invention.
Figure 5:
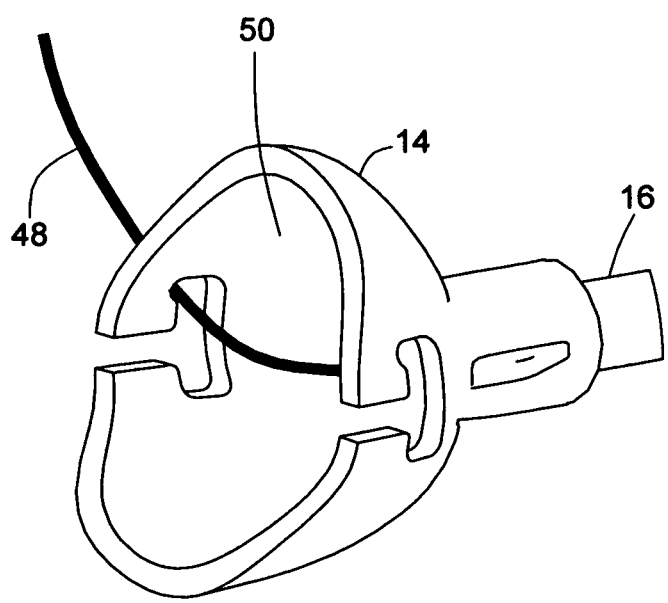
FIG. 5 is the same as FIG. 4 showing the guidewire within the retention feature.

FIGS. 4 and 5 are details of the hub 14 located at the proximal section 22 of the access sheath 10. As mentioned above, the hub 14 facilitates the insertion of medical devices into the tube or sheath 16. In facilitating this access, the hub 14 typically would take the shape of a funnel 50 with a large proximal opening which roughly decreases in diameter until the tube or sheath 16 is reached.

A common device used during medical procedures is a guidewire 48. Built into the hub 14 is a guidewire retention feature 40. The guidewire retention feature 40 consists of a first slot 42 and a second slot 44. The second slot 44 is generally situated perpendicular to the first slot 42. A detent 46 may also be included on the second slot 44. FIG. 4 shows a guidewire 48 as it may typically be placed in an access sheath. Note that in this configuration the guidewire 48 is free to move longitudinally through the passageway 26. To retain the guidewire 48, the shaft of the guidewire 48 is first passed through the first slot 42 of the hub 14, then into the second slot 44 of the hub 14. The frictional force resulting from the flexure of the guidewire 48 as it transverses the second slot 44 inhibits the longitudinal movement of the guidewire 48. If present, the detent 46 inhibits the guidewire 48 from reentering the first slot 42. Note that access to either the proximal or distal end of the guidewire 48 is not required to position the guidewire 48 into the guidewire retention feature 40. Multiple guidewire retention features 40 may be included on the hub 14 in order to manage multiple guidewires 48. Guidewire retention features 40 may be provided along the circumference of the hub 14 to allow for physician preference of guidewire 48 placement in the field of operation or to allow for right handed/left handed preferences. The guidewire retention feature 40 may also be employed to retain elongated flexible members other than guidewires.

Figures 6, 7:
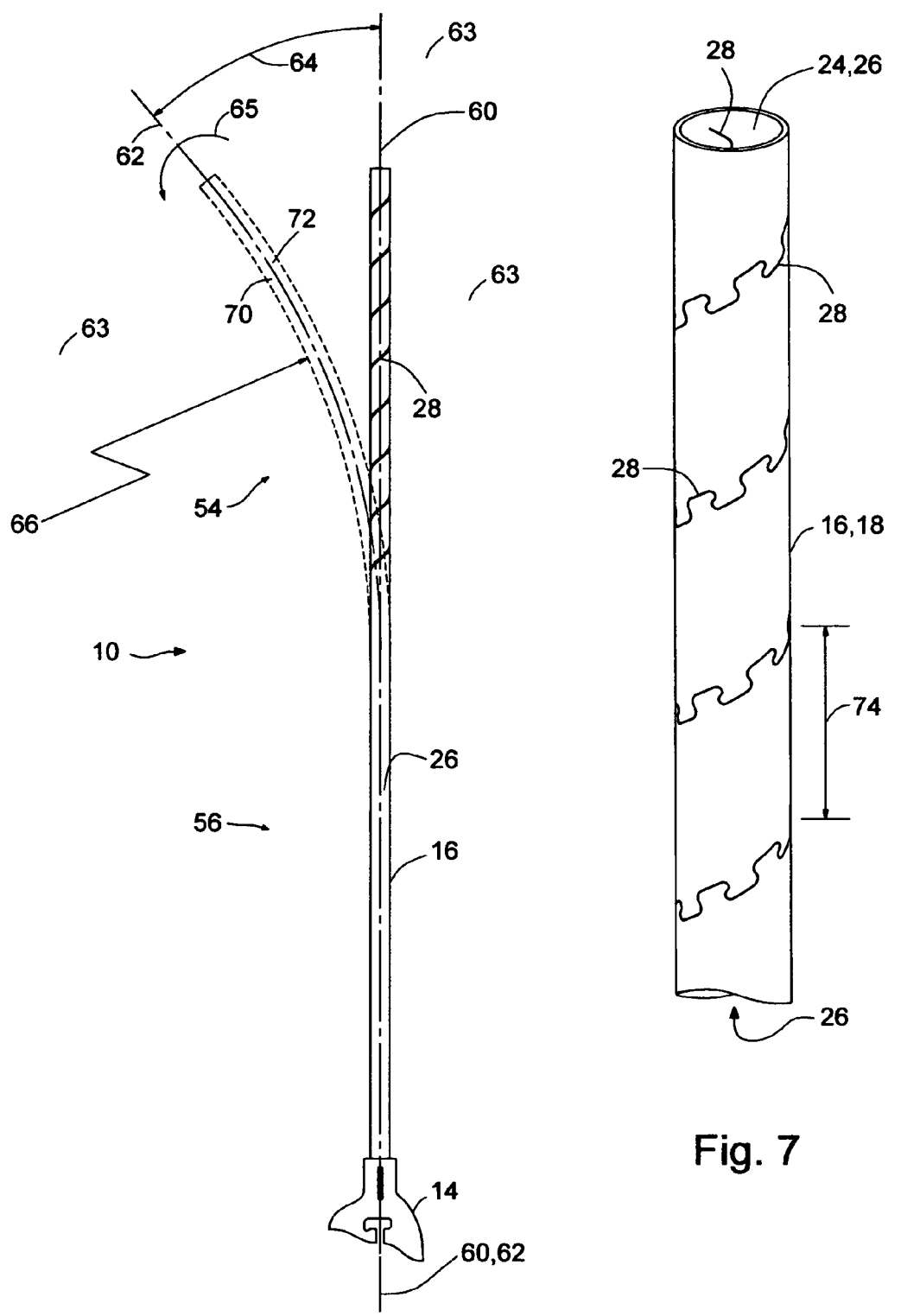
FIG. 6 is a side view of the access sheath showing the sheath in the straight or natural position and at its bend limit which is the curved position.
FIG. 7 is an enlarged isometric view of the distal end of the distal section of FIG. 6.

FIG. 6 shows the restricted flexure or bend of the distal section 20 as previously mentioned. The longitudinal axis 60 or 62 of the tube or sheath 16 proceeds from the hub 14 and through the passageway 26. The distal section 20 of the tube or sheath 16 includes one or more slots 28 cut in a generally helical pattern through the wall of the tube. The slot 28 allows a restricted flexure of the bending section 54 of the tube or sheath 16 from the longitudinal axis in the natural or straight position 60 to the longitudinal axis when bent 62. It should be noted that the natural position does not necessarily have to be straight but could be manufactured with a preset curve. When viewed from above, the plane of flexure 63 is the paper that FIG. 6 is printed on. Torque 65 is applied in this plane 63 at tip 25 which causes the bending section 54 of the access sheath 10 to deflect into bend angle 64 and bend radius 66 while the rigid section 56 of the access sheath 10 remains in the straight or natural position 60. The longitudinal axis when bent 62 splits the distal section 20 into an expansive half 72 and a compressive half 70. The nature of the slot 28 limits the amount of bend angle 64 and the bend radius 66 that the distal section 20 may exhibit. The bend radius limit of the longitudinal axis 60 or 62 is generally 3 to 4 inches or greater, preferably 6 inches or greater and optimally 12 inches or greater. The bend angle limit of the longitudinal axis 60 or 62 is generally 180° or less, preferably 90° or less and optimally 60° or less. It is noted that the nature of the slot 28 may allow multiple bend radii in potentially multiple planes. It is further noted that the slot 28 or multiple slots could extend over the entirety of the tube or sheath 16 for complete flexure of the access sheath 10.

Figure 8:
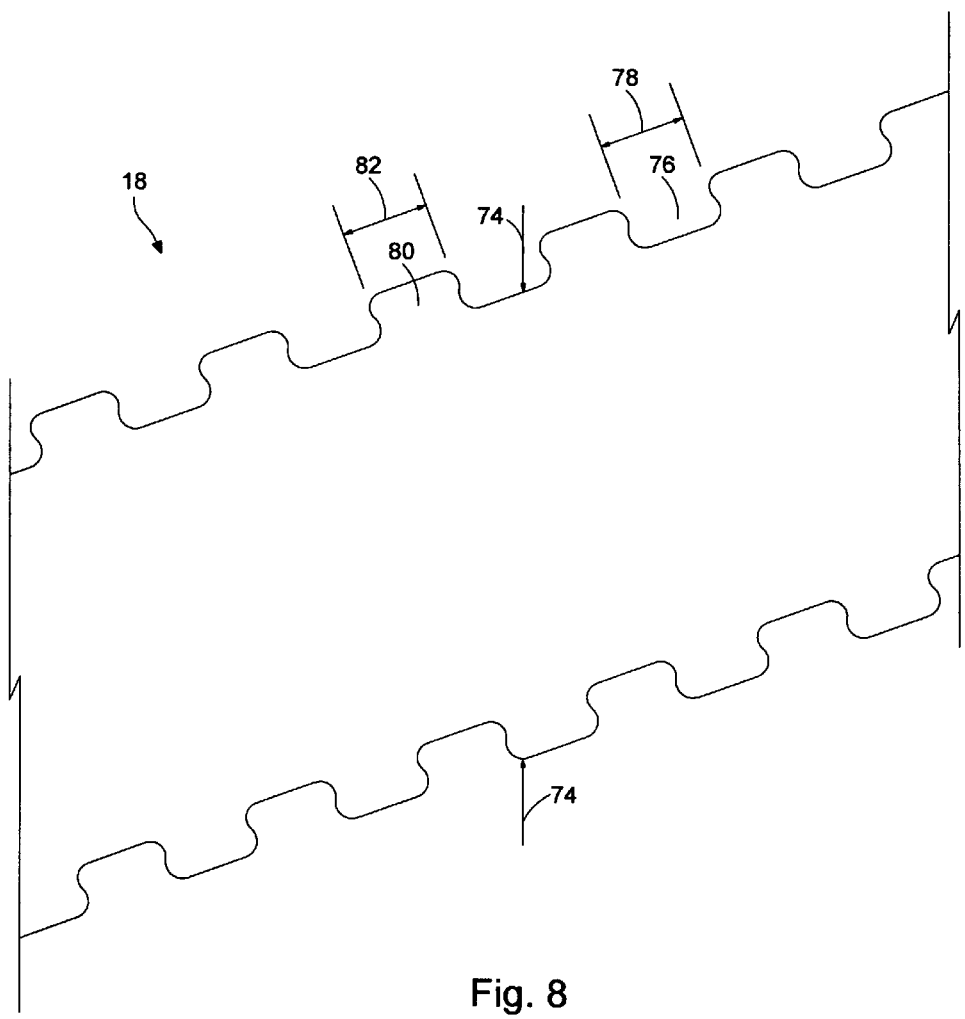
FIG. 8 is development of FIG. 7 showing a part of the solid portion of the surface rolled out into a plane.
Figure 9:
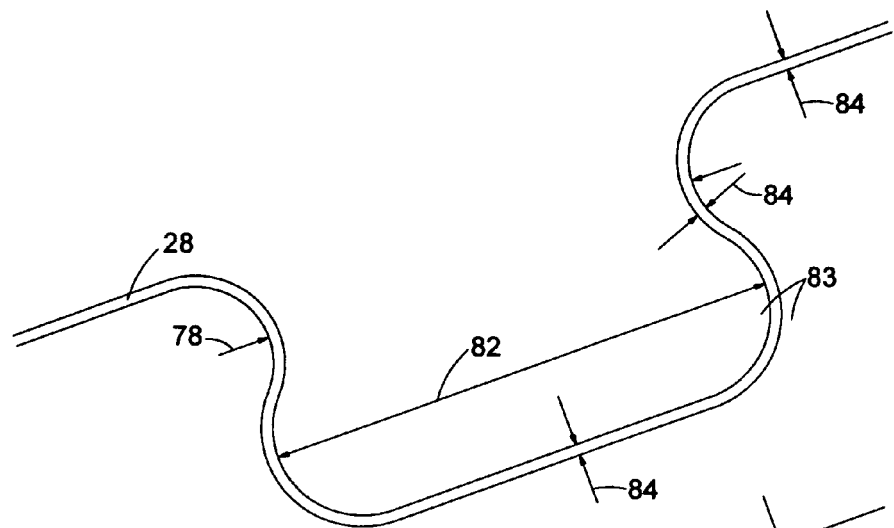
FIG. 9 is an enlarged view of a small portion of the slot shown in FIGS. 1, 3, 6 and 7. This is typically how the slot may look when the sheath is straight.
Figure 10:
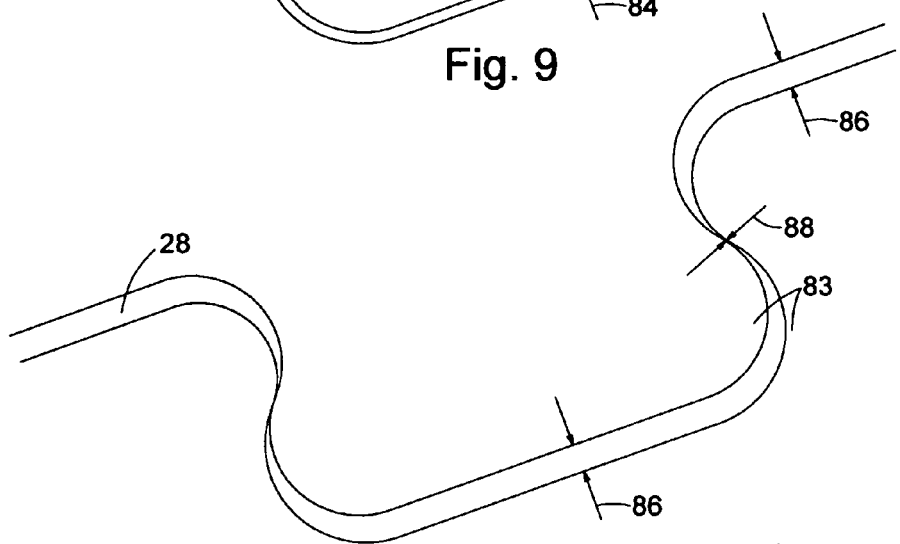
FIG. 10 is similar to FIG. 9 but shows the possible slot configuration on the expansive side of the sheath at its bend limit in FIG. 6.
Figure 11:
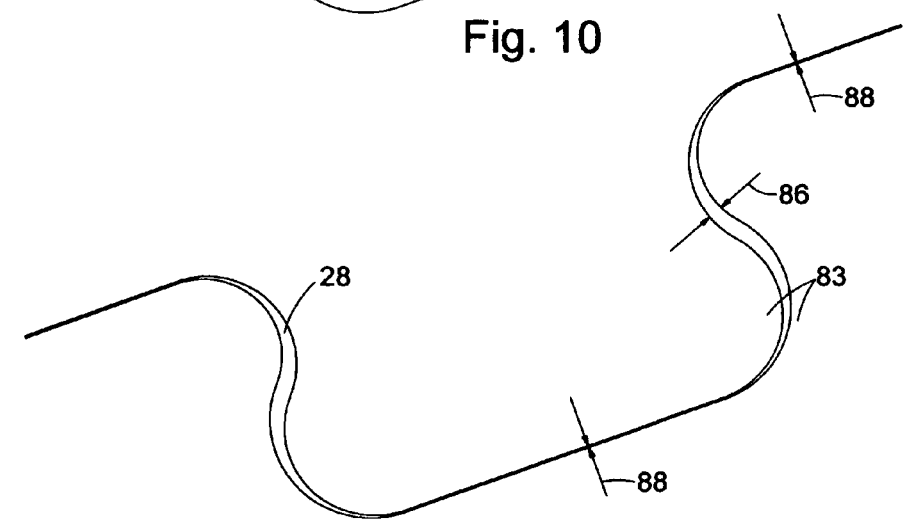
FIG. 11 is similar to FIG. 9 but shows the possible slot configuration on the compressive side of the sheath at its bend limit in FIG. 6.

FIG. 7 is a detail of the bending section 54 of the tube. One or more slots 28 originate slightly proximal to the opening 24. The slot or slots 28 continue in a generally helical orientation. The pitch of the generally helical orientation is defined by a longitudinal spacing 74. Typically the slot pattern within tubular frame 18 shown in FIG. 7 is formed using a laser to cut a slot in a rigid metallic tube or something that has a similar material or structure. The most common material being stainless steel or nitinol. FIG. 8 shows a section of the tubular frame 18 if it was opened and flattened out. Cutting the pattern from flattened stock then rolling it up would be another method of producing the tubular frame. The pattern of the slot 28 is a repetition of a serpentine path which separates the tubular frame 18 into interlocking mortises 76 and tenons 80. The mortise width 78 is less than the tenon width 82 to prevent the release of the mortise 76 from the tenon 80 when a tensional force is applied to the neighboring sections. FIG. 9 shows that slot 28 separates solid portions 83 of the tubular frame. In addition slot 28 defines a mortise 76 and tenon 80. Note that slot 28 itself has dimension. When a tension is applied as in FIG. 10 to the neighboring solid portions 83, the result is a gap width increase 86 which is limited as the gap width decrease 88 at the mortise 76 and tenon 80 tends towards zero assuming there is no coating to restrict the movement. When a compression is applied as in FIG. 11, the gap width increase 86 is limited as the corresponding gap width decrease 88 tends towards zero assuming there is no coating to restrict the movement. This limited gap width increase 86 and decrease 88 is multiplied through the plurality of the mortise 76 and tenons 80 to enable a cumulative effect upon the compressive half 70 and expansive half 72 and thus affecting a restrictive flexure or bend of the bending section 54 of the access sheath 10. It is noted that the gap width 84 of the slot 28 could be varied where smaller or larger slots 28 would respectively allow increased or decreased bend radii 66 in bending sections 54. Constantly varying thickness of slots 28 or the longitudinal spacing 74 could be used to create constantly varying bend radii 66.

FIGS. 6 and 7 show the tubular frame 18 and the sheath or tube 16 being basically the same because it is easier to show that embodiment of the invention especially without any coating. Another embodiment would be to have the tubular frame occupy only a portion the longitudinal length of sheath 16 while the remainder of the sheath could be of another construction. The bend angle 64 would be taken only on the longitudinal axis 60 and 62 within the longitudinal length of tubular frame 18.

Figure 12:
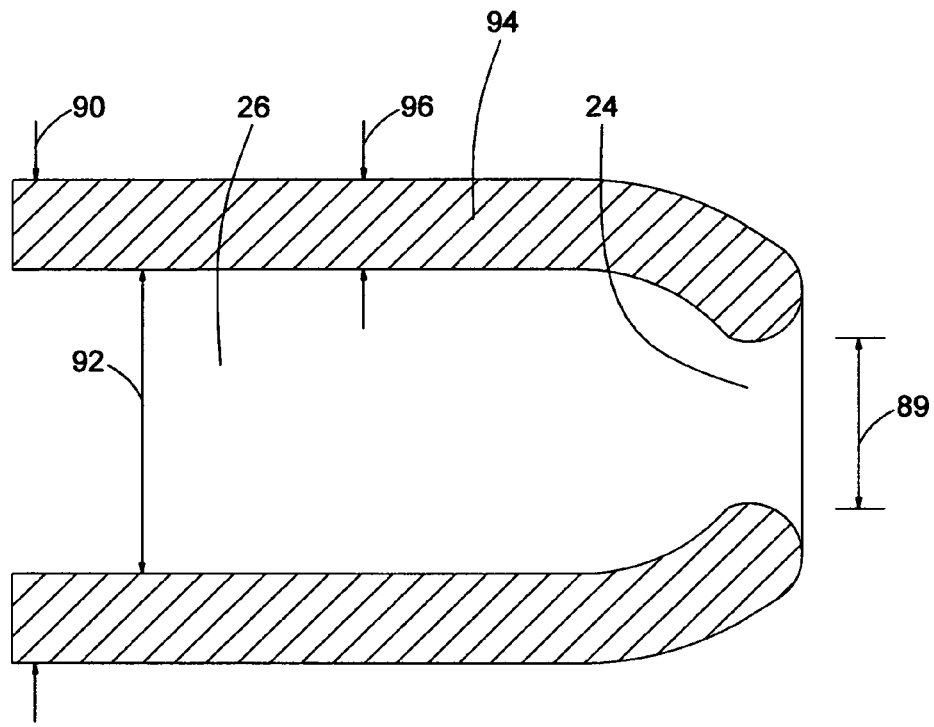
FIG. 12 is a longitudinal cross-sectional view showing another embodiment of the distal end of the distal section of FIGS. 1, 6 and 7.
Figure 13:
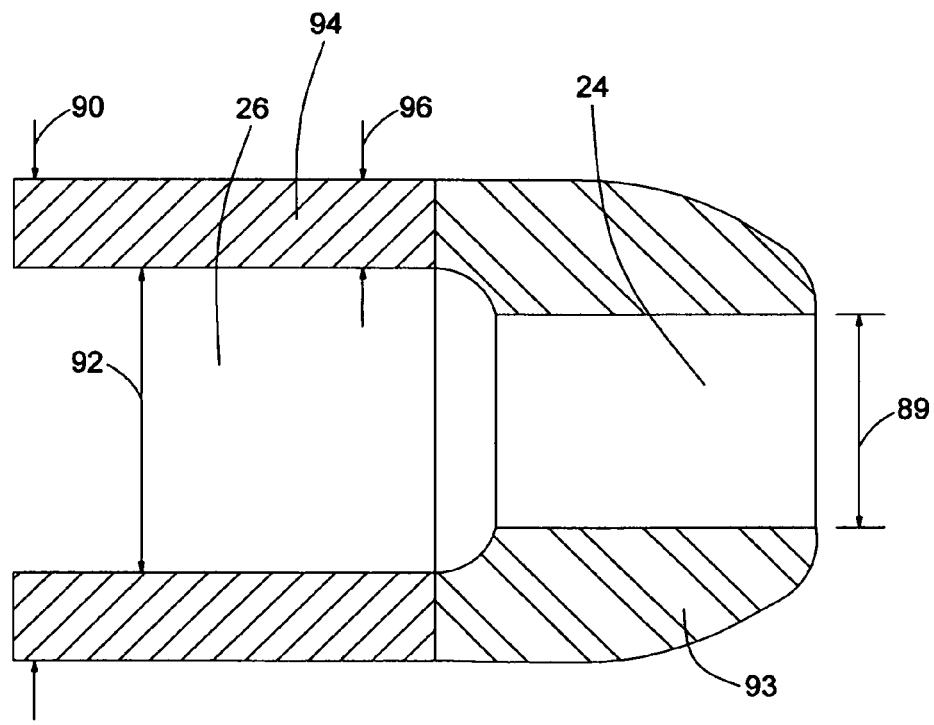
FIG. 13 is a longitudinal cross-sectional view showing yet another embodiment of the distal end of the distal section of FIGS. 1, 6 and 7.

FIGS. 12 and 13 are cross sectional details of the opening 24 of the access sheath 10 which shows several other embodiments of the invention. When a stone enters the inner diameter 92 of the passageway 26, it may become wedged or jammed and occlude the passageway 26. The creation of a reduced opening diameter 89 limits the size of stone entering the passageway 26 and ensuring that the stone will be able to fully navigate the passageway 26. Furthermore, the mating of the dilator or obturator 30 to the access sheath 10 requires clearance between the inner diameter of the tube or sheath 16 and the outer diameter of the dilator or obturator shaft. It is desirable for the fit between the opening 24 and the shaft of the dilator or obturator 30 to be as small as possible to allow a gradual transition between the two items. The gradual transition allows for minimal trauma as the assembly is inserted into the patient anatomy. In FIG. 12 a transition from the general inner diameter 92 of the tube or sheath 16 to the opening 24 is accomplished by the forming of the wall 94 causing a reduction from the outside diameter 90 to create an opening inner diameter 89 which is less than the tube's inside diameter 92. The opening inner diameter 89 should approximate the outer diameter of the shaft of the dilator or obturator 30. In FIG. 13 the inner diameter reduction is accomplished by the addition of a sheath tip 93 onto the distal end 25 of the tube 16. The sheath tip 93 could be a molded or machined item which is bonded, welded, or otherwise affixed to the distal end 25 of the tube 16. The sheath tip 93 could be of a reduced durometer to create an atraumatic tip.

FIG. 14 shows a tube or sheath 16 exhibiting a slot 28 with longitudinal spacing 74 that varies along the generally helical path. Near the opening 24 is a first rigid section 56*a*. The first rigid section 56*a* is followed by a first bending section 54*a* wherein the slot 28 has a first longitudinal spacing 74. After a longitudinal distance the longitudinal spacing 74 of the slot 28 changes into a second longitudinal spacing 74 within a second bending section 54*b*. After the bending sections, the tube or sheath 16 returns to a second rigid section 56*b*. The changing of the longitudinal spacing 74 directly affects the number of mortise 76 and tenon 80 pairings along a longitudinal length of the tube. This creates bending sections 54*a* & 54*b* with different bend radii 66. The various bend radii 66 may be designed to match the desired maximum curvature as the access sheath 10 is inserted through, or rests within, the patient anatomy. In this embodiment the bend radius limit of the longitudinal axis is generally 4 to 5 inches or greater, preferably 9 inches or greater and optimally 18 inches or greater. The bend angle limit of the longitudinal axis is generally 140° or less, preferably 50° or less and optimally 30° or less. It is noted that the number of bending sections could be increased. Furthermore, the longitudinal spacing 74 could be constantly variable to create bending sections with a constantly varying limited flexure. It may also be considered that the longitudinal spacing 74 could vary in sectors of the circumference of the tube or sheath 16 in order to vary the limited flexure in different planes.

FIG. 14*a* is an enlarged cross-sectional view of FIG. 14 taken at line A-A showing the tubular frame without coating which is an embodiment of the invention. FIGS. 14*b* and 14*c* are cross sections of the tube or sheath 16 showing possible coatings of the tubular frame 18 which is another embodiment of the invention. FIG. 14*a* shows a section of an uncoated tube or sheath 16 having a given outsider diameter 90, inside diameter 92, and wall thickness 96 defining the tubular frame 18. FIG. 14*b* shows a similar tubular frame 18, or a different longitudinal section of the previous tubular frame 18, wherein a coating 100 has been applied to the outer surface of the tubular frame 18. FIG. 14*c* shows a similar tubular frame 18, or a different longitudinal section of the previous tubular frame 18, wherein a liner 102 has been placed along the inner surface and a coating 100 has been applied to the outer surface of the tubular frame 18. This coating 100 could be a polymeric jacket that would change the bending properties of the sheath especially if the material was within the slots. A similar configuration may incorporate a liner 102 applied to the inner surface of the tubular frame 18 but no coating is applied to the outer surface. The coating 100 and/or liner 102 may be lubricious to assist in the passage of the access sheath 10 into patient anatomy or the passage of medical devices through the passageway 26. The coating 100 and/or liner 102 may be used to seal the slots 28 of the tube or sheath 16 thus limiting or eliminating the passage of fluid through the slot 28 from the inner diameter 92 of the tubular frame 18 to the outer diameter 90 of the tubular frame 18. The coating 100 and/or liner 102 may also be used to affect the stiffness of the access sheath 10. Wire reinforcement could also be incorporated to affect the bend properties of the access sheath.

FIG. 15 is a table listing physical attributes of access sheaths made by major manufacturers. Note that the invention is different from the other listed access sheaths in that the difference between the outer diameter 90 and inner diameter 92 is one French size as opposed to the typical two French sizes. This is also seen in the distal wall thickness 96 where the invention typically has a wall thickness 96 which is thinner than current competitive product. The wall is especially thin with the first listed configuration of the invention where the tubular frame 18 is uncoated or has a light surface coating such as a hydrophilic coating. The second listed configuration of the invention considers a tubular frame 18 with a coating 100 as is demonstrated in FIGS. 4*b* and 4*c*. The sheath length is similar for all listed access sheaths. The sheath construction demonstrates that sheath construction among the major manufacturers is a stainless steel coil reinforced polymeric sheath. In contrast, the current invention incorporates the bend limiting tubular frame 18.

Figure 16:
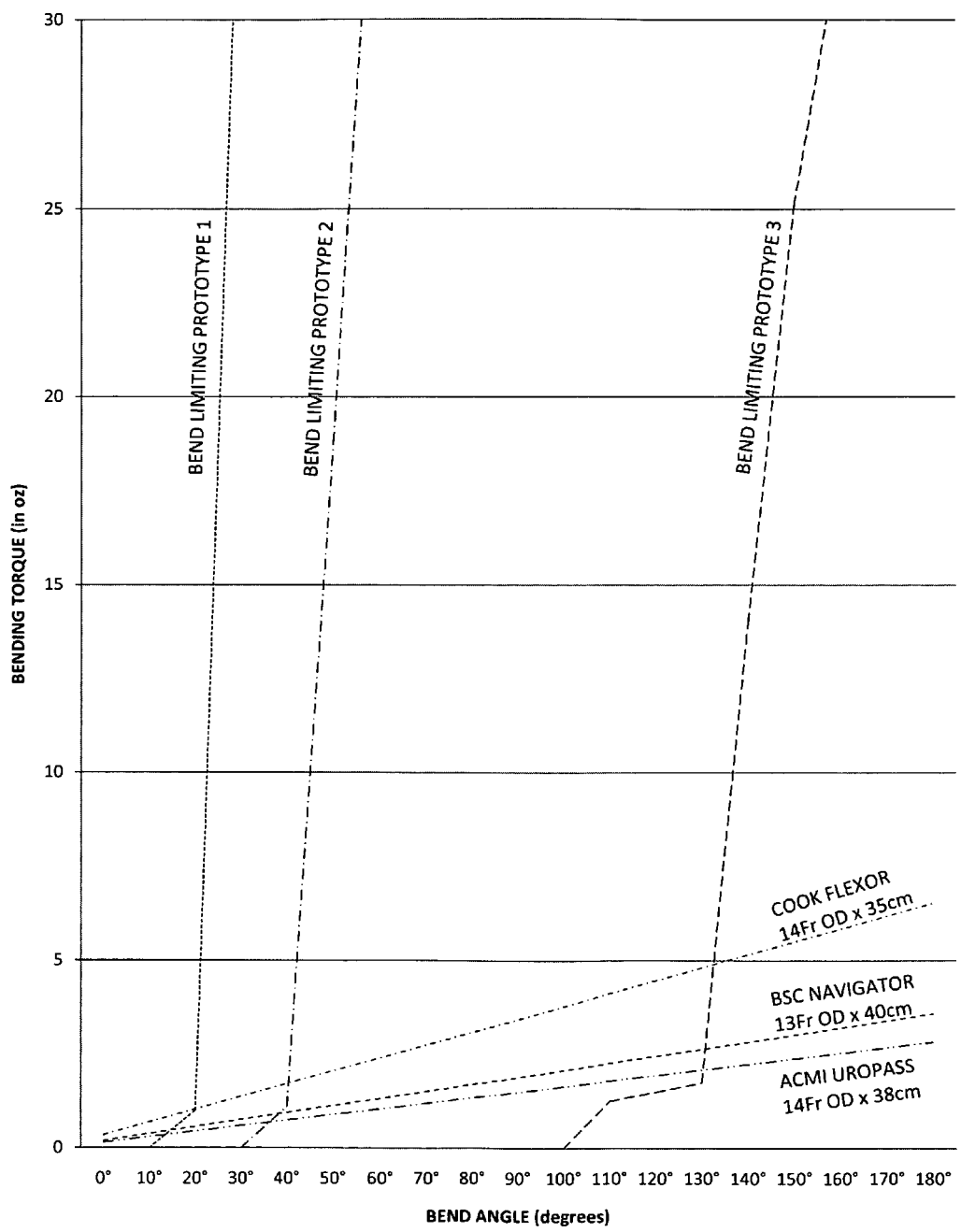
FIG. 16 is a graph showing bending torque versus bend angle. It compares some of the widely distributed access sheaths with the invention.

FIG. 16 is a graph demonstrating the relationship between the bending torque 65 of an access sheath 10 and the resulting bend angle 64 shown in FIG. 6. Data was compiled by holding the proximal section 22 at the hub 14 horizontal while applying a perpendicular torque to a gage pin that was inserted into opening 24. The resulting angle 64 at opening 24 from horizontal or natural position was recorded. As would be expected, all access sheaths required no torque to maintain the horizontal (0°) position. Raw data taken every 10° was used to compute the linear regressions plotted in FIG. 16 for the three competitive products. ACMI UroPass demonstrated the most flexibility and the Cook Flexor demonstrated increased stiffness. The graph highlights the marked difference between the competitive product and the three bend limiting prototypes of the current invention. For all three prototypes, zero bending torque was experienced for several degrees after 0°. In the case of bend limiting prototype 3, no torque was measured until an angle of 100° was reached. This lack of resistance is seen as the gap width 84 has free travel until the gap width decreased 88 reaches zero (assuming unimpeded slots). Once the gap width decreased and 88 reaches zero, the bending torque increases at a rate greater than that of the competitive product. This results in the current invention momentarily matching the bending torque of competitive product. For bend limiting prototype 1 this occurs at 15° to 20° of bend angle. For bend limiting prototype 2, this occurs at 40° of bend angle. Bend limiting prototype 3 incorporates multiple bend sections 54 as illustrated in FIG. 14. The result of the multiple bend sections 54 is that the initial period of zero bend torque, and the rapid bending torque increase, is followed by period where the rate of increase in bending torque paralleled competitive product. For all three prototypes, when the gap width decreased 88 reached zero, the prototypes experienced very rapid increases in the amount of torque per degree of bend angle. The rate of change in bending torque is much higher later in the curve as compared to earlier sections of the prototype's curve. This is what is generally considered their limit. The rate of increase could be seen as asymptotic in nature; such that the bend limiting prototypes would never be able to reach the bend angle without failure or kinking commonly and easily achieved by competitive product. For the tested prototypes, maximum bend angles were approximately 30°, 50° and 140° to 150°. All three of these prototypes would have failed (kinked) before 180°. Prototypes 1 and 2 would have failed (kinked) most likely before 60° and definitely before 90°.

Another embodiment shown in FIG. 16 is the level of bending torque that the access sheath prototypes (or tubular frame) can withstand within a bend angle of 180° or less. The maximum bending torque is generally 10 inch ounces or greater, preferably 20 inch ounces or greater and optimally 30 inch ounces or greater before kinking.

The prototypes tested were uncoated as is shown in FIG. 14a. Had the prototypes been coated, as in FIG. 14b or 14c, the bending torque at lower bend angles would likely mimic competitive product until the gap width decreased 88 reaches a point at which an asymptotic like increase in bending torque would be observed. There would be a rapid drop when at the failure point in which a kink would result.

While preferred embodiments of the present invention relate to ureteral access sheaths for endoscopic procedures in the urinary system, several other applications are envisioned as well. Examples include the retrieval of biliary stones, gall bladder stones, or other objects or tissue during the course of an endoscopic or laparoscopic procedure. The present invention might also be useful for procedures using exceedingly small diameter catheters where pushability is required but the small dimension of the catheter structure makes the transfer of longitudinal force to the tip difficult. The present invention may be embodied in other specific forms without departing from the spirit or essential attributes thereof, and it is therefore desired that the present embodiments be considered in all respects as illustrative and not restrictive.

What is claimed is:

1. A bend limiting tubular frame configured as an access sheath to be inserted into a urethra, through a urinary bladder and into a ureter, the bend limiting tubular frame comprising:

a distal end oriented toward or proximate to a distal section of said access sheath;

a proximal end oriented toward or proximate to a proximal section of said access sheath, said proximal section adapted to accept instrumentation; and a passageway extending longitudinally through the bend limiting tubular frame, said passageway having an average inner diameter sufficient to accept said instrumentation, said bend limiting tubular frame including at least one bending section of a defined maximum length comprising a slot having at least one generally helical portion, said slot having a gap width and being sized and located to define a bend limit of said bending section within said defined length of a bend radius of 6 inches or greater, at least a portion of said slot including interlocking tenons and mortises configured such that a tenon is maintained within a respective mortise in both tension and compression bending of said bending section, wherein said tubular frame is rotatable when said bending section is curved, and wherein said bending section within said defined length is able to withstand 20 inch ounces of bending torque at the bend limit without kinking.

2. The bend limiting tubular frame of claim 1 wherein a bend angle of said bending section within said defined length is limited to 60° or less or said bend radius is limited to 12 inches or more.

3. The bend limiting tubular frame of claim 1 wherein said bending section includes a plurality of radius limits.

4. The bend limiting tubular frame of claim 1 wherein said tubular frame is formed from a rigid tube.

5. The bend limiting tubular frame of claim 1, further comprising a hub having a first end coupled to said proximal section of said tubular frame, and a second end configured to accept instrumentation, said first end having a smaller sized lumen than said second end.

6. The bend limiting tubular frame of claim 1 wherein said passageway has an average inner diameter which is greater than an inner diameter at said distal end.

7. The bend limiting tubular frame of claim 1 wherein a wall surrounds said passageway and said wall comprises a wall thickness of 0.004 inch to 0.011 inch over at least a portion of said passageway.

8. The bend limiting tubular frame of claim 1 wherein at least a portion of said distal section of said sheath has an outside diameter of 12 Fr. to 16 Fr. and comprises a sheath length of 20 cm to 55 cm.

9. The bend limiting tubular frame of claim 1 wherein the bending section is configured to prevent buckling when said bend limiting tubular frame is advanced across an internal cavity of the bladder even if resistance is encountered during advancement.

10. The bend limiting tubular frame of claim 1 wherein at least a portion of the slot comprises a serpentine configuration.

11. The bend limiting tubular frame of claim 1, wherein said bend limiting tubular frame lacks a separable outer sheath around said slot.

12. A bend limiting ureteral access sheath to be inserted into a urethra through an internal cavity of a urinary bladder and into a ureter comprising:

a tubular frame having a slot within a bendable section of said tubular frame, said slot including a generally helical portion, said bendable section having a defined maximum length and formable into a curve when bent between opposite ends of said defined maximum length, said defined maximum length sufficient to span the internal cavity of the bladder from the urethra to the ureter, wherein at least a portion of said slot includes interlocking tenons and mortises configured to limit said bendable section in tension and in compression to a bend radius of 6 inches or more and configured such that a tenon is maintained within a respective mortise in both tension and compression bending of said bending section;

a hub having a first end coupled to a proximal section of said tubular frame, and a second end configured to accept instrumentation, said first end having a smaller sized lumen than said second end;

an opening located at a distal end of said tubular frame, said opening sized to enable passage of said instrumentation therethrough; and a passageway extending longitudinally therethrough from said proximal end to said opening at said distal end;

wherein said bendable section is rotatable when said bendable section is curved, and wherein said bending section within said defined length is able to withstand 20 inch ounces of bending torque at the bend limit without kinking.

13. The bend limiting ureteral access sheath of claim 12 wherein a bend angle of said bendable section within said defined maximum length is limited to 60° or less or said bend radius is limited to 12 inches or more.

14. The bend limiting ureteral access sheath of claim 12 wherein said bendable section includes a plurality of radius limits.

15. The bend limiting ureteral access sheath of claim 12 wherein said tubular frame is formed from a rigid tube.

16. The bend limiting ureteral access sheath of claim 12 wherein said hub further includes a guidewire retention feature.

17. The bend limiting ureteral access sheath of claim 12 wherein at least some portion of said tubular frame is rigid.

18. The bend limiting ureteral access sheath of claim 12 wherein a wall surrounds said passageway and said wall comprises a wall thickness of 0.004 inch to 0.011 inch over at least a portion of said passageway.

19. The bend limiting ureteral access sheath of claim 12 wherein at least a portion of said distal section of said sheath has an outside diameter of 12 Fr. to 16 Fr and comprises a sheath length of 20 cm to 55 cm.

20. The bend limiting uretral sheath of claim 12 wherein said limit of said bendable section within said defined length of a bend radius of 6 inches or greater provides rigidity to said frame to allow longitudinal transmission of force so that said access sheath can be advanced into a small orifice.

21. The bend limiting ureteral access sheath of claim 12 wherein at least a portion of the slot comprises a serpentine configuration.

22. The bend limiting ureteral access sheath of claim 12, further comprising:

a dilator releasably coupleable to said access sheath, said dilator having a proximal end releasably coupleable to said hub, a shaft configured to fit within said passageway, and a distal end having a tip configured to fit within and extend beyond said opening located in said distal end of said tubular frame.

23. The bend limiting ureteral access sheath of claim 12, wherein said tubular frame has a generally constant outer cross-sectional size.

24. The bend limiting ureteral access sheath of claim 12, wherein said opening in said distal end of said tubular frame is aligned with a longitudinal axis of said passageway when said access sheath is unbent.

\* \* \* \* \*